United States Patent [19]

Chew, III

[11] 4,149,805

[45] Apr. 17, 1979

[54] METHOD AND APPARATUS FOR MEASURING KEROGEN CONTENT OF OIL SHALE

[75] Inventor: Randall T. Chew, III, Grand Junction, Colo.

[73] Assignee: Occidental Oil Shale, Inc., Grand Junction, Colo.

[21] Appl. No.: 764,859

[22] Filed: Feb. 2, 1977

[51] Int. Cl.² .................. G01J 3/50; G01N 21/48
[52] U.S. Cl. ......................... 356/416; 23/230 EP
[58] Field of Search .......... 356/70, 186, 201, 204–206, 356/209–212; 23/230 EP; 250/301, 339–341, 372

[56] References Cited

U.S. PATENT DOCUMENTS

| 3,232,711 | 8/1966 | Senyk et al. ................. 356/38 X |
| 4,009,962 | 3/1977 | Lauer et al. ................. 350/70 X |
| 4,030,837 | 6/1977 | Kojima et al. .................. 356/209 |

Primary Examiner—F. L. Evans
Attorney, Agent, or Firm—Christie, Parker & Hale

[57] ABSTRACT

The kerogen content of oil shale is measured by illuminating the surface of a solid piece of oil shale so that the amount of light not absorbed by the oil shale is reflected from the illuminated surface. A monochromatic portion of the reflected light is sensed, the wavelength of the sensed light being within the absorption band for kerogen in oil shale. The amount of light absorbed by the piece of oil shale is proportional to its kerogen content, and the amount of sensed reflected light, which is inversely proportional to kerogen content, is converted into a measurement of kerogen content. To avoid wide variations in measured kerogen content, caused by non-uniform kerogen distribution within the sample being analyzed, reflected light is integrated over an area of the sample likely to have numerous varves containing kerogen.

27 Claims, 9 Drawing Figures

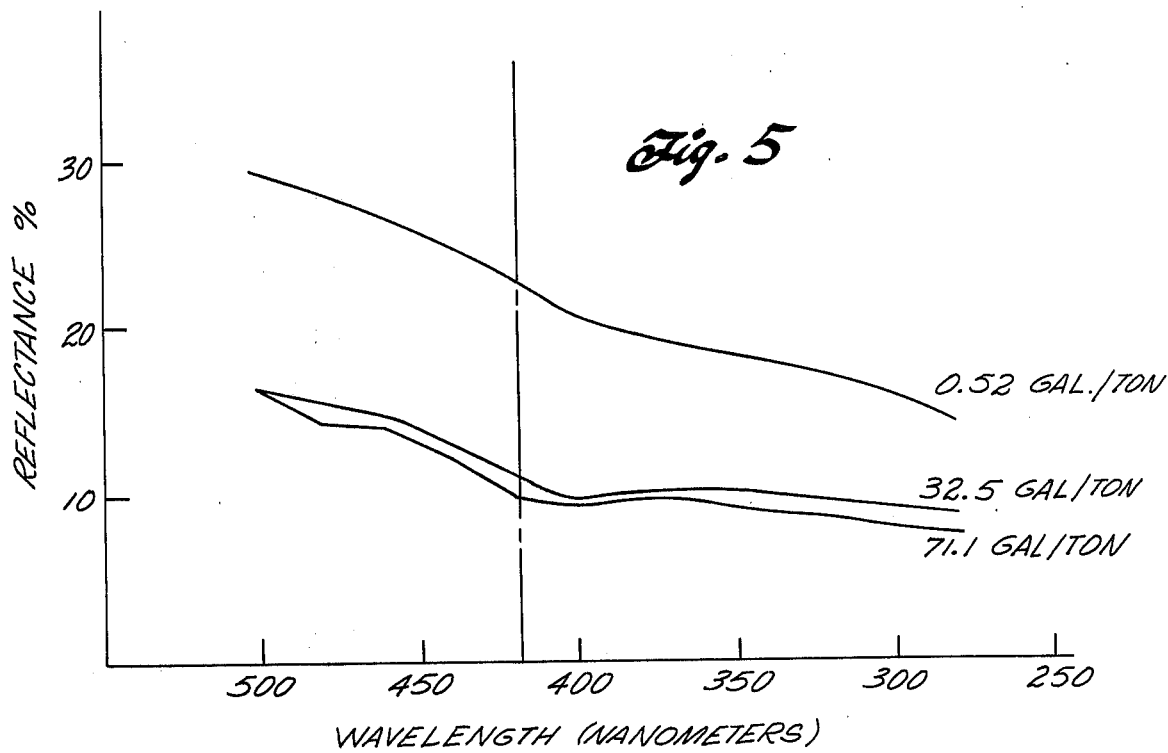
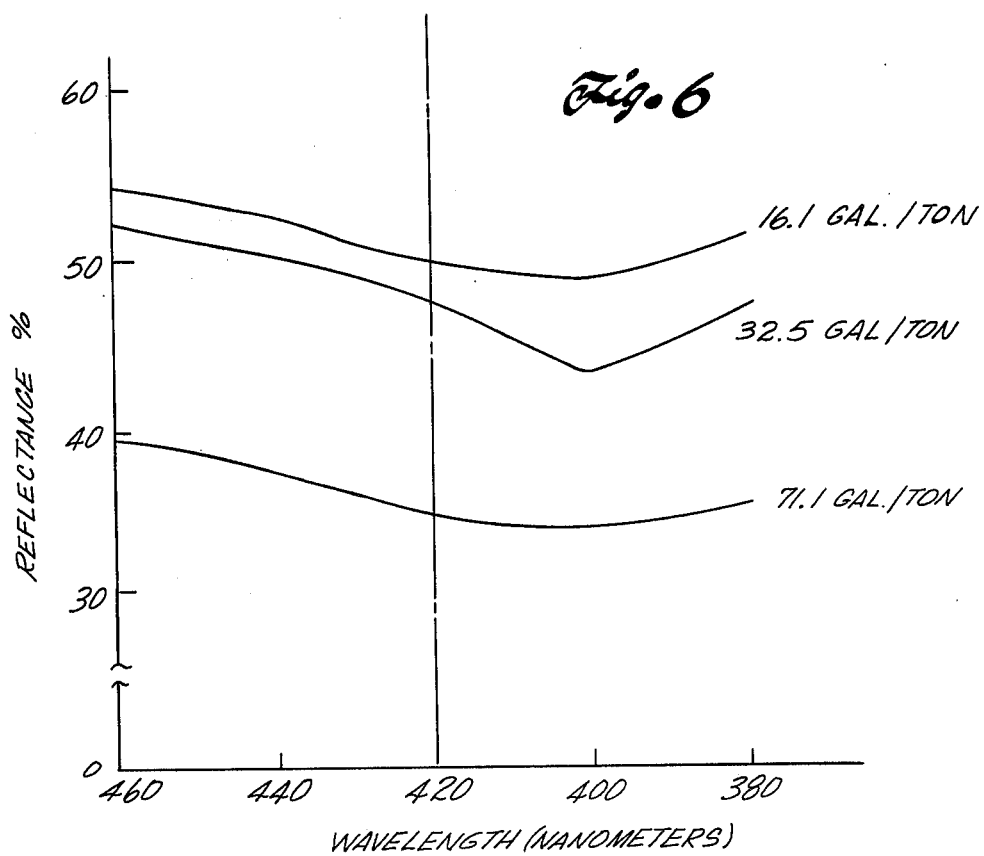

METHOD AND APPARATUS FOR MEASURING KEROGEN CONTENT OF OIL SHALE

BACKGROUND

This invention relates to a method and apparatus for measuring the kerogen content of oil shale. The kerogen analysis of this invention can be performed immediately without requiring laboratory analysis and calculations, or destructive techniques.

Vast untapped reserves of oil entrapped in oil shale exist in this country as well as other locations throughout the world. Increased attention is being devoted to the exploitation of oil shale because of the current need for new energy sources.

The term "oil shale" as used in the industry is in fact a misnomer, because it is neither shale, nor does it contain oil. It is a sedimentary formation comprising marlstone deposits interspersed with layers containing an organic polymer called "kerogen" which upon heating decomposes to produce carbonaceous liquid and gaseous products. It is the formation containing kerogen that is called "oil shale" herein, and the carbonaceous liquid product is called "shale oil".

Oil shale deposits occur in generally horizontal beds, and within a given bed there are an extremely large number of generally horizontal deposition layers containing kerogen known as "varves". The varves typically are non-uniformly dispersed throughout a given bed. In the higher grade oil shales, the varves are commonly cemented together into relatively thick, compact layers. The lower grade oil shales have much thinner varves spaced apart through the bed. For example, a core sample taken from a typical bed may vary from thick, solid oil shale sections to layered sections having the appearance of poker chips. In the core, small layers or nodules of other minerals and rock materials are sometimes found interspersed between the varves containing kerogen. Typical of these other minerals are nahcolite, dawsonite, other salines, dolomite, mudstone, sandstone, tuffs, analcite and bentonite.

Techniques for preparing shale oil for retorting generally comprise explosively expanding a subterranean oil shale formaion to form a fragmented, permeable mass of oil shale particles. Shale oil then may be recovered from the particles by in situ retorting techniques, or by retorting in surface retorts, for example.

Prior to preparing the oil shale for retorting, the formation is explored to determine the locations within the formation containing the highest grades of oil shale. Core samples are taken from the formation and subjected to laboratory analysis to determine the kerogen content of the sample. One such analytical technique is the "Fischer assay" in which a sample customarily weighing 100 grams and representing one foot of core is subjected to controlled laboratory analysis involving grinding the sample into small particles which are placed in a sealed vessel and subjected to heat at a known rate of temperature rise to measure the kerogen content of the core sample. Kerogen content is usually stated in units of "gallons per ton", referring to the number of gallons of shale oil recoverable from a ton of oil shale heated in the same manner as the Fischer analysis.

Such analytical techniques are generally done in laboratories far from the drilling site. This causes a considerable delay before analytical results are available to field personnel conducting the exploration tests. Thus, immediate field decisions on the progress of the exploration program cannot be based on accurate analyses of core samples.

The present invention provides a method and apparatus for rapidly determining the kerogen content of oil shale. The invention does not require calculations or destructive laboratory techniques characteristic of the Fischer assay and other known methods for measuring kerogen content. The invention makes it possible to accurately analyze a core sample of oil shale in the field and still have the core sample available for other purposes, such as corroborating laboratory measurements to be conducted later at a more convenient time. Thus, field decisions on the progress of the exploration program can be made immediately, rather than waiting for several days, which is a common delay for current kerogen analysis techniques.

SUMMARY OF THE INVENTION

According to a presently preferred embodiment of the invention, the kerogen content of a solid sample of the oil shale is measured by a method and apparatus for illuminating a surface of the sample to reflect the light not absorbed by the sample. The amount of light absorbed by the sample is proportional to the amount of kerogen contained in the oil shale sample and is measured by detecting the amount of light reflected from the illuminated surface. The light which is detected is essentially monochromatic light within the absorption band for kerogen in oil shale. The amount of monochromatic light detected is indicated as a value proportional to the kerogen content of the sample.

The wavelength of said monochromatic light is selected to provide sensitive measurements of reflected light in response to variations in kerogen content over the range of kerogen concentration likely to be encountered in the particular type of oil shale under analysis. A given core sample will reflect a specific amount of light when the sample is illuminated with light at a given wavelength. The detected monochromatic light is converted into a measurement of kerogen content based on a corresponding measurement of the amount of light reflected at the same wavelength from a reference oil shale sample having a known kerogen content.

In analyzing an elongated core sample of oil shale, a selected surface area of the core sample is illuminated. The amount of light reflected from the illuminated area is detected and converted into a measurement of kerogen content in the illuminated area of the oil shale. To avoid wide variations in the measurement of kerogen content along a given sample, the amount of light reflected from the oil shale is integrated over an area likely to include numerous varves containing kerogen. In one form of the invention, reflected light is integrated by measuring the amount of light reflected from an illuminated area of selected size large enough to encompass many varves.

These and other aspects of the invention will be more fully understood by referring to the following detailed description and the accompanying drawings.

DRAWINGS

FIG. 5 is a graph illustrating the relationship between light wavelength and light reflectance from oil shale core samples of varying known kerogen content, using magnesium oxide as a standard for 100% reflectance;

FIG. 6 is a graph illustrating the relationship between light wavelength and light reflectance from oil shale core samples of varying known kerogen content, using barren marlstone as a standard for 100% light reflectance;

DETAILED DESCRIPTION

Figure 1:
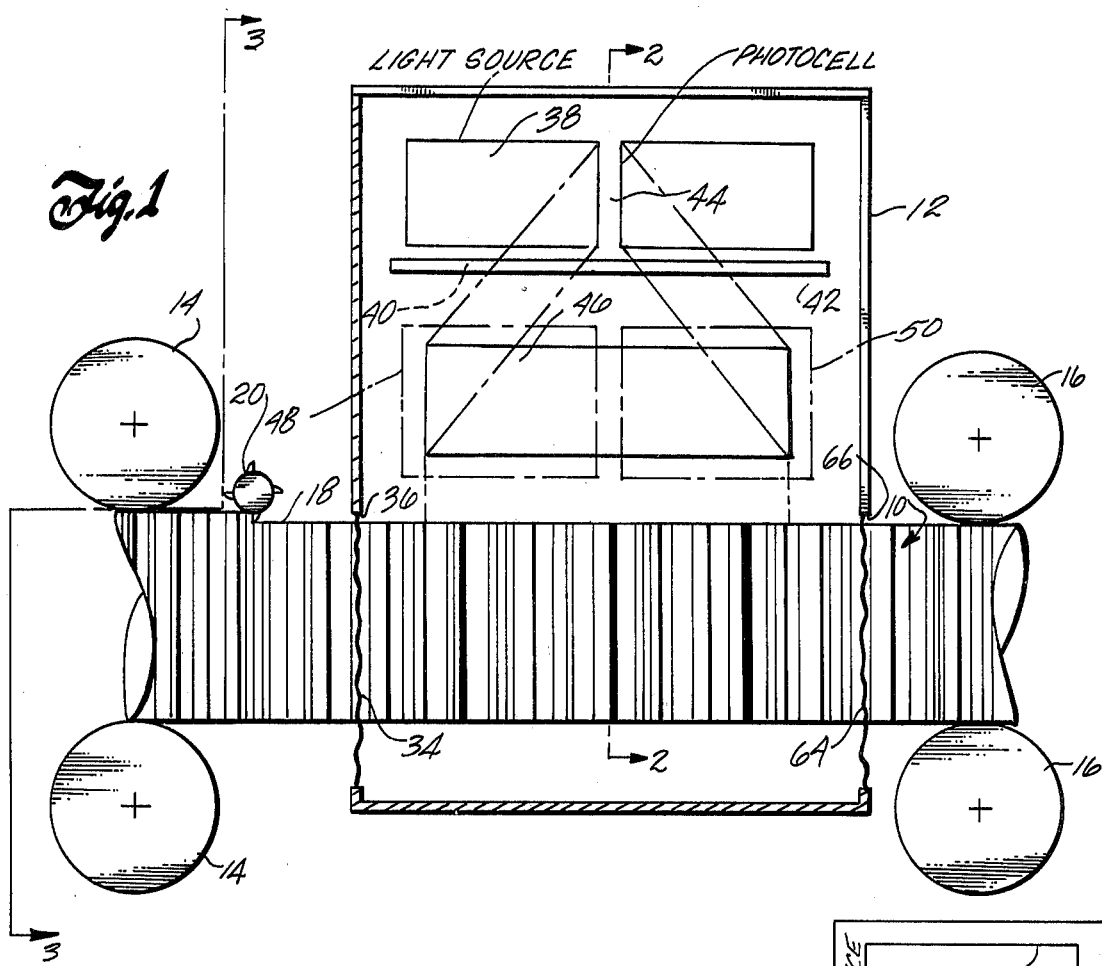
FIG. 1 is a fragmentary, schematic elevation view illustrating a presently preferred method and apparatus for measuring the kerogen content of an oil shale core sample according to principles of this invention.

This invention is based on a recognition that the kerogen content of oil shale is proportional to the amount of light, of a selected wavelength, absorbed by the oil shale. A solid core sample of oil shale can be immediately and non-destructively analyzed for kerogen content, according to a presently preferred embodiment of this invention, by illuminating a surface of the sample with light having a monochromatic component within the absorption band for kerogen in oil shale, and detecting the amount of light absorbed by the sample. Preferably, the amount of light absorbed is detected by sensing the amount of light reflected by the illuminated surface of the core sample. The reflected light is inversely proportional to the amount of light absorbed and also inversely proportional to the kerogen content in the portion of the sample being illuminated. The amount of said monochromatic light reflected from the illuminated surface is detected and converted into a measurement proportional to the kerogen content of the sample. The amount of kerogen in the sample is determined by comparing the amount of monochromatic light reflected from the sample with the amount of monochromatic light, at the same wavelength, reflected from a reference piece of oil shale having a known kerogen content.

The term "light" is used herein to mean light energy not only in the visible spectrum, but also light extending into the ultraviolet and infrared spectra. The term "monochromatic light" is meant to include light of a discrete wavelength, or at least light in a narrow wavelength band, say of 25 nanometers or less. The term "solid sample of oil shale" is defined herein to mean an intact piece of oil shale as distinguished from powdered. The solid piece can have some cracks or delaminations as long as they do not absorb light to the extent of producing appreciably misleading results.

The kerogen content of a sample of oil shale is measured by detecting the amount of monochromatic light absorbed by the sample, in which the monochromatic light has a wavelength within the absorption band for the kerogen contained in the particular type of oil shale under analysis. The presently preferred wavelength for analyzing oil shale from the Piceance Creek Basin in Colorado and Utah is within the range of about 260 to about 500 nanometers, i.e., at the low end of the visible spectrum and part of the near ultraviolet spectrum. The preferred discrete wavelength is about 420 nanometers. This wavelength is preferred because of its relatively good sensitivity in discerning variations in kerogen content over a relatively wide range of potential kerogen concentrations in a piece of oil shale.

The presently preferred wavelength of the light used to measure kerogen content was determined according to the following procedure. Smooth surfaces of identical configuration and size were formed on several core samples of oil shale having known kerogen contents. The surface of each sample was then illuminated with monochromatic light, and the amount of light reflected from the surface of each sample was sensed by a photocell. The wavelength of the monochromatic light source was varied in increments of 20 nanometers, and reflectance for each increment was sensed. In one test, samples ranging in known kerogen content from 0.52 gallons per ton to 71.1 gallons per ton were analyzed. The known kerogen content of the samples was initially determined over one foot of core using Fischer assay techniques. The samples were then examined using wavelengths ranging from about 280 to about 500 nanometers. Magnesium oxide was used as a standard for 100% reflectance. A Beckman DU Spectrophotometer was used to measure reflectance from a 0.75-inch diameter circle on each sample. The test results are illustrated in the graph shown in FIG. 5. The results showed a consistent decrease in the amount of light reflected (reflectance) from the surface of the oil shale as the grade or kerogen content of oil shale increased. The difference in measured reflectance between the highest and lowest assays was generally greatest at a wavelength range of about 420 nanometers (indicated in phantom line in FIG. 5), although the test results also showed good sensitivity at a wavelength of about 480 nanometers.

In a separate test, the reflectance of several samples ranging in known kerogen content from 16.1 gallons per ton to 71.1 gallons per ton was conducted using a marlstone sample of zero kerogen content as a standard for 100% reflectance. The samples were examined using wavelengths varied in increments of 20 nanometers in a range of about 380 to 460 nanometers. The test results are illustrated in FIG. 6 and again showed a trend toward decreasing reflectance with increasing kerogen content. The greatest sensitivity in reflectance measurements among the samples tested generally occurred at a wavelength of about 420 nanometers (indicated in phantom line in FIG. 6).

Thus, a given core sample will reflect a specific amount of light when the sample is illuminated with light at a given wavelength, and the presently preferred wavelength for light used to measure kerogen content in the type of oil shale under analysis is about 420 nanometers. This wavelength generally exhibits a good range of light absorption (or reflectance) as a function of kerogen assay, i.e., the greatest sensitivity to changes in kerogen concentration for the samples tested.

Figure 2:
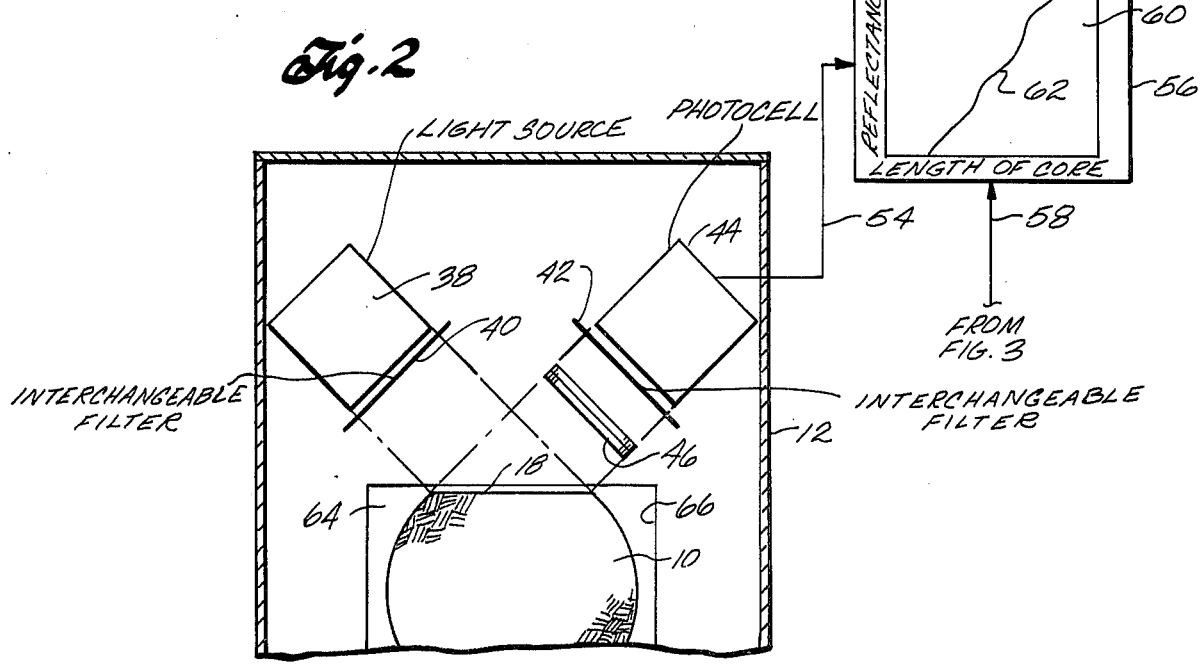
FIG. 2 is a schematic cross-sectional view taken on line 2—2 of FIG. 1.
Figure 3:
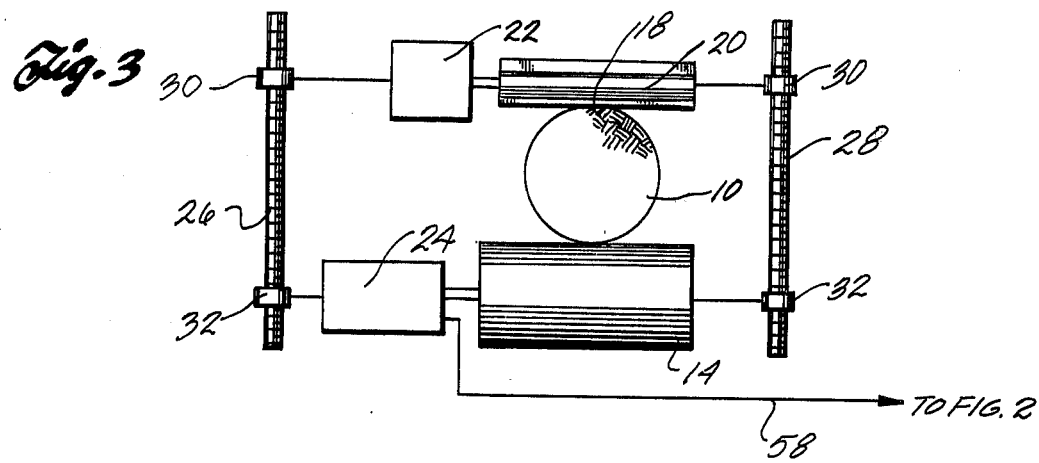
FIG. 3 is a schematic cross-sectional view taken on line 3—3 of FIG. 1.

FIGS. 1 through 3 illustrate a presently preferred field instrument for rapidly measuring the kerogen content of oil shale. The field instrument also can be used to measure the amount of any material contained in a solid core sample, as long as the material being analyzed absorbs or reflects light in proportion to its concentration in the core sample when a surface of the sample is illuminated with light having a monochromatic component within the absorption band of the material being analyzed.

The following description of the field instrument will be in the context of its use in measuring the kerogen content of an elongated cylindrical core sample 10 of solid oil shale obtained by standard rock core drilling procedures from the Piceance Creek Basin. The core sample 10 is moved lengthwise through a stationary, essentially light-tight housing 12 in which the core sample is illuminated by a light source having the desired monochromatic component necessary to analyze kerogen content. The core sample is moved through the housing 12 by drive rollers 14 which apply pressure to the top and bottom surfaces of the core sample to force the sample through an entrance to the housing 12. Idler rollers 16 spaced longitudinally from the drive rollers 14 apply pressure to the top and bottom of the core sample 10 and support the core sample as it passes away from the housing 12.

Prior to moving the core sample 10 through the housing 12, a smooth reflective surface 18 of selected configuration is formed along the top surface of the core sample. The smooth reflective surface 18 reduces light scattering from subsequent illumination of the surface. Preferably, the reflective surface 18 is continuously formed by a rotary milling cutter 20 which mills a narrow, flat surface on the core sample 10 immediately before the core sample is fed through the housing 12. A tungsten carbide tipped milling cutter is preferred to minimize effects of wear by the oil shale. It will be understood that the milling cutter is illustrated schematically with drawings. The milling cutter 20 forms a flat surface of uniform width, preferably about ⅜ to about ½ inch wide, along the length of core sample 10. As shown best in FIG. 3, a drive motor 22 rotates the milling cutter 20, and a separate drive motor 24 rotates the drive rollers 14.

Alternatively, a diamond trim saw may be used to form a flat, smooth reflective surface lengthwise along the core sample. Further, the reflective surface can be formed by cutting a core sample in half lengthwise along its diameter.

The flat, smooth surface 18 need not be formed if all core samples to be analyzed are of the same surface configuration and are relatively smooth so that appreciable light scattering is avoided.

The relative spacing between the lower drive roller 14 and the milling cutter 20 is adjustable to accommodate core samples of different diameter. The spacing between the upper and lower drive rollers 14 also can be adjusted. FIG. 3 schematically illustrates a presently preferred position-adjusting mechanism, although a variety of structures may be used to adjust the spacing between a milling cutter and its drive means. The position-adjusting mechanism illustrated in the drawings includes upright threaded shafts 26 and 28 adjacent opposite edges of the core sample 10. A pair of upper position-adjusting devices (represented schematically at 30) are engaged with the upper portions of the threaded shafts 26, 28 on opposite sides of the core sample. The upper position-adjusting devices 30 can be a pair of sleeves loosely fitted around the threaded shafts 26, 28 and engaged with adjusting nuts for being turned relative to the threaded shafts to adjust the position of the milling cutter 20 and its drive motor 22 relative to both the core sample 10 and the lower drive roller 14. A pair of similar lower position-adjusting devices (represented schematically at 32) are engaged with the lower portions of the threaded shafts 26, 28. The lower position-adjusting devices 32 are engaged with adjusting nuts for being turned relative to the threaded shafts 26, 28 to adjust the position of the lower drive roller 14 relative to the core sample 10, the milling cutter 20, and the upper drive roller 14. A similar adjusting mechanism (not shown) adjusts the elevation of the lower idler roller 16 and the spacing between the upper and lower idler rollers 16.

After passing under the milling cutter 20, the core sample 10 passes through a first light-tight curtain 34 covering an entrance opening 36 in the housing 12. An electric light source 38 located in the upper interior portion of the housing 12 illuminates a selected area on the flat reflective surface 18 as the core sample travels through the housing 12. The light source 38 generates light (as defined above) which includes a wavelength within the light absorption band for kerogen in oil shale. In the presently preferred form of the invention, the light source 38 is an ultravoilet fluorescent lamp. The light from the lamp passes through a first filter 40 disposed between the light source and the reflective surface 18 of the core sample 10. The filter 40 is a narrow bandpass filter which passes monochromatic light, preferably light having a wavelength of about 420 nanometers. Alternatively, a monochromatic light source, without light filtering means, can be used, as long as the wavelength of the light produces a useful degree of sensitivity, in terms of measured reflectance, to a relatively wide range of kerogen concentrations likely to be encountered in oil shale.

As illustrated in FIG. 2, the light source 38 is mounted at an angle with respect to a vertical plane through the longitudinal axis of the reflective surface 18 formed on the core sample 10. Light which is not absorbed by the core sample 10 is reflected from the reflective surface 18 and passes through a second filter 42 prior to being sensed by a photocell 44. The second filter 42 passes the same wavelength as that passed by the first filter 40.

Alternatively, only one light filter can be used. In this instance, the filter is on the photocell side of the instrument to ensure preventing any stray light from being sensed by the photocell.

The filters 40 and 42 are removably mounted in the housing 12 so that they can be replaced with other filters for passing monochromatic light of other selected wavelengths. For example, oil shale from different locations can have different light absorption bands dependent upon the type of kerogen contained in them, and core samples of materials other than oil shale also will have different light absorption bands depending upon the chemical component being analyzed; and the field instrument herein enables the user to test analyze the core sample for light absorption at selected wavelengths and select the filter passing the wavelength which yields results having the greatest sensitivity in terms of reflectance measurements for the particular core sample under analysis.

The photocell 44 is located within the upper interior portion of the housing 12. The photocell 44 detects only the light reflected from the illuminated area of the core sample. The photocell 44 produces an electrical output having a magnitude directly proportional to the amount of sensed reflected light, and therefore inversely proportional to the amount of light absorbed by the core sample. The relationship between reflectance (absorption) and kerogen concentration is essentially linear over a relatively wide range of kerogen concentrations likely to be encountered in oil shale. Hence, the measurement of light reflectance provides a reliable indication of kerogen content for a given core sample.

FIGS. 1 through 3 illustrate a presently preferred system for integrating the amount of light reflectance (absorption) over a selected area of the core sample. The light integration system is used because of the typically non-homogenous concentration of kerogen in any given sample of oil shale. That is, kerogen is often dispersed in randomly spaced apart varves of different concentrations and random width along the length of a core sample of oil shale. If a relatively narrow area of the core sample is illuminated at any given time, then resulting reflectance measurements can exhibit relatively wide variations in kerogen content along the length of the core sample. The light integration system senses illumination from a relatively wide area likely to contain numerous varves of kerogen to avoid large amplitude variations in measured kerogen content due to the typically non-uniform distribution of kerogen. This system gives a spatial integration of kerogen content in a sample of oil shale.

In the integration system of FIGS. 1 through 3, the light source 38 is elongated and is mounted so as to illuminate the entire width, and a one-foot length, of the core sample reflective surface 18. The length of one foot is chosen to correspond to the one-foot length of core often used to determine kerogen content by Fischer assay techniques. In integrating the light over one-foot lengths, the core sample can be illuminated intermittently over the one-foot lengths, with the amount of reflected light for each one-foot length being intermittently sensed and recorded. However, other lengths of the core sample 10 can be illuminated by the light source 38, or the light source 38 can be used in combination with a lens system (not shown) to direct incident light onto a selected area of the core sample. Further, the light integration can be continuous as well as intermittent.

The presently preferred light integration system also includes a lens 46 (illustrated schematically) between the core sample and the second filter 42. The lens 46 focuses on the photocell 44 the light reflected from the illuminated area of the core sample. Preferably, the lens 46 is a cylindrical lens for focusing on the photocell 44 all of the light reflected from the essentially rectangular, one-half inch wide, one-foot long area illuminated by the light source 38. The entire amount of focused light sensed by the photocell 44 at any time is proportional to the average amount of reflectance along the one-foot length of core at that time. A one-foot length of core is likely to contain numerous varves containing kerogen. Spatial integration of the reflectance over this length of core sample produces a measurement of the average kerogen content of the one-foot sample, independently of whether the core sample contains a highly non-uniform kerogen distribution.

If it is desired to analyze only a narrow length of core, or if the core sample to be analyzed is less than one foot long, a pair of spaced-apart movable blinders 48 and 50 (illustrated in phantom lines in FIG. 1) can be used to block the passage of light from the core sample to part of the surface of the lens 46. The blinders 48 and 50 can be spaced apart by any selected distance to adjust the area of illumination sensed by the photocell.

Light integration systems other than the light focusing lens system of FIGS. 1 through 3 can be used. For example, a suitably arranged system of mirrors (not shown) can be located in the housing to collect light reflected from a relatively larger area of the core sample and focus the light on the relatively smaller area of the photocell 44.

The photocell 44 produces a continuous electrical output having a magnitude proportional to the instantaneous amount of reflected light sensed by the photocell. The electrical output from the photocell can be used to drive a recorder which records measured reflectance, or the photocell output can be converted into a measurement of light absorption. In either of these instances the recorder is preferably calibrated to display percent reflectance or absorption based on the corresponding reflectance or absorption of a reference sample of oil shale of known kerogen concentration. Alternatively, the recorder can be calibrated to provide a direct reading of kerogen content, in gallons per ton, for example.

In the presently preferred system, the electrical output from the photocell 44 is connected by a line 54 to a chart recorder 56 which produces a continuous reading of light reflectance relative to the length of the core sample. The core sample drive motor 24 generates an output over a line 58 connected to the chart recorder 56 to synchronize movement of the paper drive (not shown) for the recorder chart 60 with the length of the core traveling through the housing 12. The recorder produces a trace 62 on the chart 60 in which reflectance from the photocell 44 is displayed on the Y axis of the chart relative to the length of the core, which is displayed along the X axis of the chart.

After being illuminated by the light source 38, the core sample 10 continuously passes through a second light-tight curtain 64 covering an exit opening 66 of the housing 12. The light-tight curtains 34 and 64 allow use of oversized entrance and exit openings 36 and 66, respectively, to accommodate core samples of different diameters.

Figure 4:
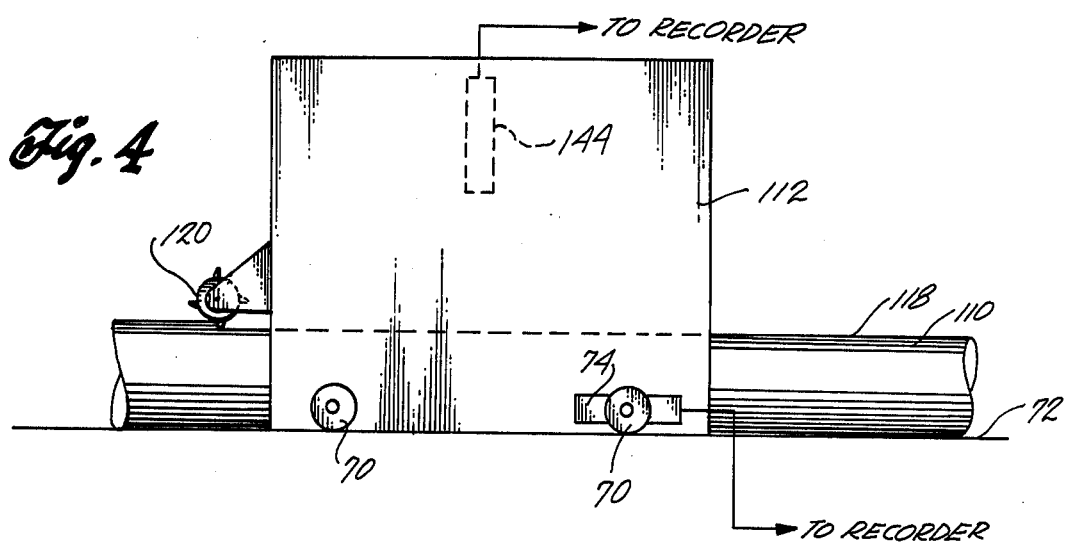
FIG. 4 is a fragmentary, schematic elevation view illustrating an alternate method of scanning the length of a core sample to measure kerogen content.

FIG. 4 schematically illustrates an alternate system for measuring kerogen content of a core sample 110 of oil shale. The alternate system includes a movable light-tight housing 112 using the same optical and electronic components described for the system illustrated in FIGS. 1 through 3. The movable system measures reflected light while traveling along the length of a core sample 110 maintained in a stationary position. The movable housing 112 is mounted on wheels 70 which roll on a flat substrate surface 72, such as a wood panel. A milling head 120 travels with the movable housing 112 to mill a narrow, flat reflective surface 118 along the top edge of the core sample 110 prior to the housing passing over the milled surface. A transducer 74 senses rotation of one of the rollers 70 of the housing 112 and generates an electrical output proportional to the longitudinal distance traveled by the housing. The output from the transducer 74 is connected to a chart recorder (not shown) along with an output signal from a photocell 144 in the housing 112. The chart recorder provides a measurement of light reflectance, or its equivalent, relative to the length of the core sample being analyzed. Means can be provided in the system of FIG. 4 to vary the elevation of the substrate surface 72 relative to the photocell 144, and other optical equipment within the housing 112, to accommodate core samples of different sizes.

Thus, in each of the systems described above, the position of the core sample can be adjusted relative to the optical system so that the reflective surfaces 18 and 118 will always be in a proper position to receive illumination over a selected area and so that the photocells receive only the light reflected from the selected area of illumination.

In using the field instrument illustrated in FIGS. 1 through 3, reflectance from a "reference" oil shale core sample is first measured to give a base line for the recorder or other monitoring system used. The reference core sample preferably comprises a barren piece of oil shale having a composition and grain size closely resembling the oil shale to be analyzed, but containing no kerogen. A magnesium oxide standard for 100% reflectance also can be used. A flat reflective surface is initially milled along the top edge of the reference core sample. The core sample is then passed through the housing 12 and into the path of filtered light from the light source 38. As described above, the light passing through the filter 40 is monochromatic, with the wavelength selected within the absorption band for kerogen in oil shale (preferably 420 nanometers). The light reflected from the reference core sample is measured by the photocell 44, and the reflectance from the reference sample establishes a scale reading of 100% (zero light absorption) for future measurements.

A large number of core samples of oil shale having a known kerogen content, say from previous chemical tests or the like, are analyzed using the same procedures and same monochromatic light wavelength as for the reference core sample. The reflectance of each core sample having a known composition is measured by the photocell 44, and these measurements are plotted, preferably in a graph showing the relationship between percent reflectance of each sample versus the known kerogen content of the sample. The graph can be used to determine the kerogen content of any core sample having an unknown kerogen content by simply measuring the reflectance from the surface of the core sample.

Figure 7:
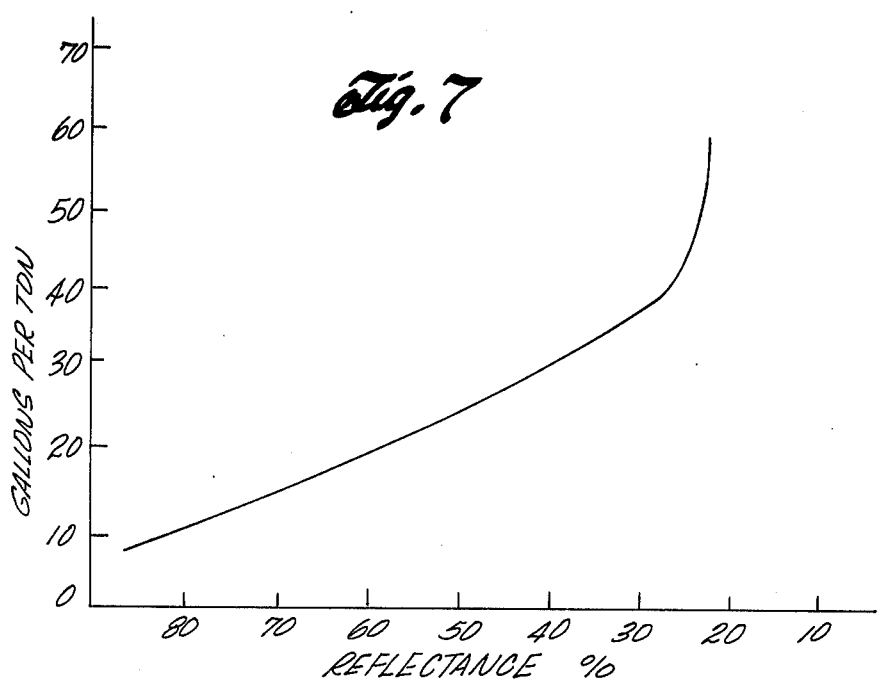
FIG. 7 is a graph illustrating the relationship between light reflectance and kerogen content of a core sample of oil shale.

FIG. 7 shows a graph obtained from measuring the reflectance of a number of oil shale core samples of known kerogen content. The samples were analyzed using Fischer assay techniques to determine their actual kerogen content. The reflectance measurements plotted were determined using oil shale reflectance at 420 nanometers wavelength with barren marlstone as the standard. The graph is a composite of data points derived from analyzing 24 core samples of varying kerogen content; and although some relatively high variations on opposite sides of the curve were present, the graph illustrates that there is a definite relationship between decreasing reflectance and increasing kerogen content up to about 40 to 45 gallons per ton at about 27% reflectance. Sensitivity of the tests were considered good in that 17 of the 24 tests yielded data points within 2 gallons per ton or 3 nanometers from the composite curve shown in FIG. 7. The graph illustrated in FIG. 5 can be used to determine the kerogen content of any core sample of unknown kerogen content if the core sample is analyzed with the same procedures and wavelength used to develop the graph in FIG. 7.

In the preferred monitoring system for the instruments illustrated in FIGS. 1 through 4, the recorder 56 plots percent reflectance as a function of the length of the core sample. The graph shown in FIG. 7 is then used to convert the percent reflectance measurements into measurements of kerogen content.

Figure 8:
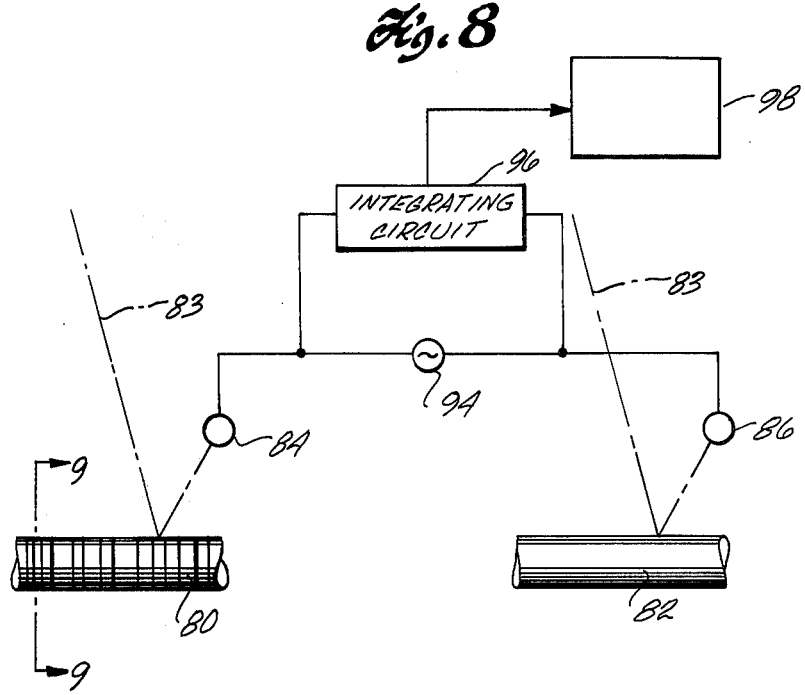
FIG. 8 is a schematic elevation view illustrating an alternate method for measuring the kerogen content of an oil shale core sample.
Figure 9:
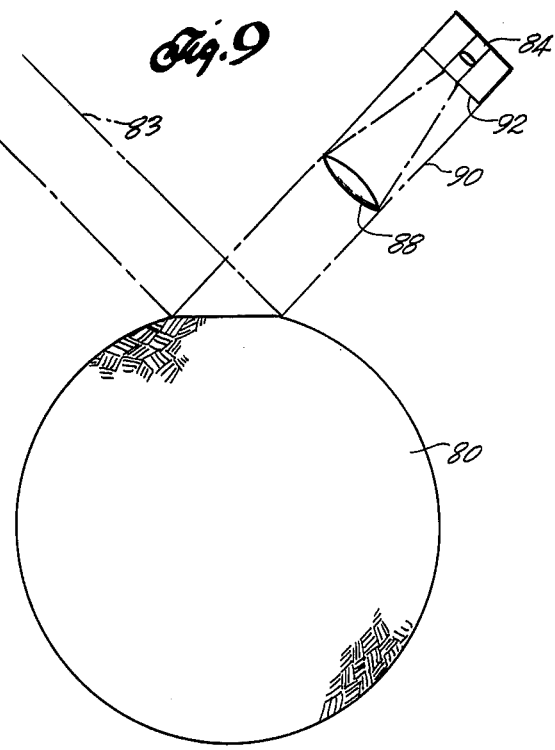
FIG. 9 is a schematic elevation view, partly in cross-section, taken on line 9—9 of FIG. 8.

FIGS. 8 and 9 illustrate an alternate form of the invention in which a core sample 80 of unknown kerogen content is continuously compared with a reference core sample 82 having a known kerogen content. Preferably, the reference core sample 82 is a barren piece of oil shale having zero kerogen content which produces a reference measurement of 100% reflectance along the length of the sample. The light source for illuminating each sample, as indicated by lines 83, can be white light from ambient sunlight, or an unfiltered light source, or a source of monochromatic light within the absorption band for kerogen in oil shale.

The reflectance from the unknown core sample 80 is sensed by a photocell 84, and the reflectance from the reference core sample 82 is sensed by a separate photocell 86. As represented for the unknown core 80 in FIG. 9, light reflected from each core sample passes through a corresponding lens 88 mounted at the front of a separate light-tight housing 90. The lenses focus reflected light on the corresponding photocells. A narrow bandpass filter 92 filters the light reflected from each sample to expose the photocells to monochromatic light having a wavelength sensitive to changes in kerogen content. As described above, the preferred light has a wavelength of 420 nanometers.

The photocell 84, together with its related focusing and filtering system, scans the length of the unknown core sample 80. Preferably, the photocell 86 and its related focusing and filtering system remains stationary to produce a constant zero standard reflectance reading. The two light sensing systems produce corresponding measurements of the instantaneous illumination sensed by the photocells. The output from each photocell is continuously fed to a null instrument 94, such as a galvanometer, which compares the instantaneous amount of light reflected from each core sample. Hence, increases in kerogen content of the unknown sample 80 are detected as increased deviations between the reflectance measurements from the two core samples.

The system illustrated in FIG. 8 includes means for integrating reflectance with respect to time, as opposed to the spatial integration system illustrated in FIGS. 1 through 4. In the system of FIG. 8, the output from the null instrument 94 is fed to an electrical integration circuit 96 which, in turn, produces an electrical output fed to a recorder 98. The integration circuit 96 can be any of a variety of electrical circuits capable of integrating, over a selected time interval, the reflectance measurements produced by the photocells 84 and 86. The integrating circuit 96 may include a time delay for sampling reflectance measurements during a time interval related to the amount of time required for the reflectance measuring system to travel a selected distance along each core sample. The magnitude of the output from the integration circuit 94 is proportional to the average amount of reflectance sensed during the selected time interval. This avoids wide variations in reflectance measurements produced by non-homogenous kerogen distribution, as discussed above. The recorder 98 produces a continuous plot of integrated reflectance relative to the length of the core sample 80.

Thus, the invention makes it possible to obtain a quantitative, non-destructive analysis of the amount of a chemical component contained in a core sample, such as the kerogen content of oil shale. The analysis requires no calculations once the instruments are calibrated. The instruments can be used on core samples obtained directly from core drilling techniques, and allows workmen in the field to immediately analyze chemical content, rather than subjecting the core sample to laboratory tests which cause delays and may be destructive to the core sample. Thus, decisions on the progress of the core drilling program can be made in the field immediately after the core is recovered from the underground formation.

I claim:

1. A method for measuring the kerogen content of oil shale comprising:
    illuminating a surface of a sample of oil shale;
    reflecting from said surface light not absorbed by the sample;
    sensing reflected light having a wavelength within the absorption band of kerogen in oil shale; and
    indicating the amount of sensed light as a measurement proportional to the kerogen content of the sample.

2. The method according to claim 1 including sensing light having a wavelength within the range of from about 260 to about 500 nanometers.

3. The method according to claim 1 including sensing light having a wavelength of about 420 nanometers.

4. The method according to claim 1 including sensing a monochromatic portion of said reflected light.

5. The method according to claim 4 including passing the monochromatic portion of the reflected light through a narrow bandpass filter, and sensing said monochromatic light.

6. The method according to claim 1 including illuminating the sample with monochromatic light having a wavelength within the absorption band of kerogen in oil shale, and sensing monochromatic light reflected at the same wavelength.

7. The method according to claim 1 including sensing light reflected from a selected area of the sample likely to contain a plurality of varves containing kerogen.

8. The method according to claim 7 including sensing light having a wavelength within the range of about 260 to about 500 nanometers.

9. The method according to claim 7 including integrating the reflected light to sense the average amount of light reflected from the selected area.

10. The method according to claim 1 including measuring the amount of light reflected from the surface of a reference piece of oil shale; measuring the amount of light reflected from the surface of said sample of oil shale; and comparing the two measured amounts of light to produce an indication representative of the kerogen content of the sample.

11. A method of analyzing the kerogen content of oil shale comprising performing the illuminating, reflecting and sensing steps of claim 1 on a first sample of oil shale having a known kerogen content; performing the illuminating, reflecting and sensing steps of claim 1 on a second sample of oil shale having an unknown kerogen content; using the amount of reflected light sensed from the first sample as a reference; and comparing the amount of reflected light sensed from the second sample with the reference to determine the kerogen content of the second sample.

12. A method for measuring the kerogen content of oil shale comprising:
    illuminating a surface area of a solid oil shale sample likely to contain a plurality of varves containing kerogen;
    reflecting from the illuminated surface area light not absorbed by said area of the sample;
    detecting an essentially monochromatic portion of said reflected light having a wavelength within the absorption band of kerogen in oil shale; and
    indicating the amount of detected light as a measurement proportional to the kerogen content of the sample.

13. The method according to claim 12 including passing the monochromatic portion of the reflected light through a narrow bandpass filter, and thereafter detecting said monochromatic light.

14. The method according to claim 13 including detecting reflected light within a wavelength range of from about 260 to about 500 nanometers.

15. The method according to claim 13 including detecting reflected light having a wavelength of about 420 nanometers.

16. The method according to claim 12 including detecting the amount of reflected light by integrating the light reflected from said surface area, and indicating the integrated amount of light.

17. The method according to claim 12 including illuminating the surface with monochromatic light having a wavelength within the absorption band of kerogen in oil shale, and detecting the amount of said monochromatic light reflected from the surface of the sample.

18. Apparatus for measuring the kerogen content of oil shale comprising:
    means for mounting a solid sample oil shale;
    means for illuminating a surface area of the oil shale sample likely to contain a plurality of varves containing kerogen;
    means for reflecting from the illuminated surface area light not absorbed by said area of the sample;
    means for detecting an essentially monochromatic portion of said light reflected from the surface area of the oil shale sample, said reflected light having a wavelength within the absorption band of kerogen in oil shale; and
    means for indicating the amount of detected light as a measurement proportional to the kerogen content of the sample.

19. Apparatus acording to claim 18 including a narrow bandpass filter, and means for passing the reflected light through the narrow bandpass filter to isolate said monochromatic light.

20. Apparatus according to claim 19 including means for detecting reflected light within a wavelength range of from about 260 to about 500 nanometers.

21. Apparatus according to claim 20 including means for detecting reflected light as a wavelength of about 420 nanometers.

22. Apparatus according to claim 18 including light integrating means for producing an output representative of the average amount of light reflected from said illuminated area; and means for indicating said output as a value proportional to the kerogen content in said illuminated area.

23. Apparatus according to claim 22 including means for detecting reflected light within a wavelength range of from about 260 to about 500 nanometers.

24. Apparatus according to claim 18 including means for generating a first output representative of the amount of light reflected from a reference piece of oil shale of known kerogen content; and in which the light sensing means produces a second output representative of the amount of light reflected from the surface of said sample; and in which the indicating means includes means for comparing the first and second outputs to produce an indication representative of the kerogen content of said sample.

25. Apparatus according to claim 18 including means for sensing reflected light with respect to the length of an elongated core sample of oil shale; and means for indicating the amount of sensed reflected light as a value proportional to the kerogen content of the sample.

26. Apparatus for measuring the kerogen content of oil shale comprising:
- a source of light for illuminating a surface of a sample of oil shale;
- first light filtering means disposed between the light source and the sample to illuminate the sample with filtered monochromatic light having a wavelength within the absorption band of kerogen in oil shale;
- light sensing means;
- second light filtering means disposed between the sample and the light sensing means to filter light reflected from the sample and to expose the light sensing means to monochromatic light of essentially the same wavelength as the light passed by the first light filtering means;
- means for mounting a sample of oil shale for reflecting from a surface thereof an amount of light not absorbed by the sample from the light source to the light sensing means; and
- means for indicating the amount of sensed light as a measurement proportional to the kerogen content of the sample.

27. Apparatus according to claim 26 including means for generating a first output representative of the amount of light reflected from a reference piece of oil shale of known kerogen content; and in which the light sensing means produces a second output representative of the amount of light reflected from the surface of said sample; and in which the indicating means includes means for comparing the first and second outputs to produce an indication representative of the kerogen content of the sample.

* * * * *